United States Patent [19]

Wetegrove et al.

[11] Patent Number: 5,593,850

[45] Date of Patent: Jan. 14, 1997

[54] MONITORING OF INDUSTRIAL WATER QUALITY USING MONOCLONAL ANTIBODIES TO POLYMERS

[75] Inventors: Robert L. Wetegrove, Winfield, Ill.; Krishna Balakrishnan, Richmond; Richard E. Bruehl, San Francisco, both of Calif.

[73] Assignee: Nalco Chemical Company, Naperville, Ill.

[21] Appl. No.: 132,600

[22] Filed: Oct. 4, 1993

Related U.S. Application Data

[63] Continuation-in-part of Ser. No. 752,746, Aug. 30, 1991, abandoned, and Ser. No. 786,154, Oct. 31, 1991, abandoned.

[51] Int. Cl.[6] ................................... G01N 33/531
[52] U.S. Cl. .......................... 435/7.92; 435/7.9; 435/975; 436/547; 436/548; 436/39; 530/388.9; 530/389.8
[58] Field of Search ..................... 435/7.1, 7.9, 7.92, 435/975; 436/547, 548, 39, 815, 518; 530/388.9, 389.8

[56] References Cited

U.S. PATENT DOCUMENTS

| | | | |
|---|---|---|---|
| 4,486,530 | 12/1984 | David et al. | 435/7.1 |
| 4,704,440 | 11/1987 | Goulding et al. | 535/376 |
| 4,752,443 | 6/1988 | Hoots et al. | 422/13 |
| 4,756,881 | 7/1988 | Hoots et al. | 422/13 |

OTHER PUBLICATIONS

M. Sela, *Handbook of Experimental Immunology*, ed. by D. M. Weir, Blackwell, Oxford: 1.2 (1978).

M. Steward *Immunology*, ed. by I. Roitt, J. B. Lippincott, Philadelphia: 7.1 (1989).

*Handbook of Experimental Immunology*, vol. 1 Immunochemistry (D. M. Wier, ed.) 4th edition, Blackwell Scientific Publications (1986).

Wang et al., "Artificial Organs and the Immune Response", in *Polymeric Materials and Artificial Organs*, Ed. by Gebelein, American Chemical Society, Washington, D.C. (1984).

Sudi et al., Kieler Milchietschafliche Forschugsberichie vol. 40, pp. 179–203 (1988) "Studies on the development of an immunoassay for the group-specific detection of the diethyl ester of phosphates, thiophosphates, dithiophosphates and phosphonates".

*Primary Examiner*—Christina Y. Chan
*Assistant Examiner*—Lora M. Green
*Attorney, Agent, or Firm*—Robert A. Miller; James J. Drake; Patricia A. Charlier

[57] ABSTRACT

The invention provides methods and compositions for monitoring chemicals used to prevent corrosion in industrial water containers. The invention is useful for chemicals such as polymers, in particular water soluble, vinyl polymers. Monoclonal antibodies are used in assays to determine the presence or concentration of the chemicals in a fluid, in particular water used in industrial systems.

14 Claims, 13 Drawing Sheets

1

MONITORING OF INDUSTRIAL WATER QUALITY USING MONOCLONAL ANTIBODIES TO POLYMERS

The present application is a continuation-in-part of U.S. application Ser. Nos. 07/752,746, filed Aug. 30, 1991, now abandoned and Ser. No. 07/786,154, filed Oct. 31, 1991, now abandoned the respective contents of which are hereby incorporated by reference.

BACKGROUND OF THE INVENTION

The invention relates generally to monoclonal antibodies directed toward polymers used to prevent accumulation of mineral deposits in containers for industrial water. These polymers include water-soluble, vinyl polymers such as polyacrylate and sulfonated copolymers of polyacrylic acid and acrylamide. The invention also relates antibody assays for the detection of the polymers. Methods for the detection and monitoring of polymers in commercial water systems are used to optimize treatment of the water to prevent mineral deposits.

Preservation of containers used for holding water for commercial purposes requires removal of mineral deposits. For example, as described in U.S. Pat. Nos. 4,756,881 and No. 4,752,443, water-soluble sulfonated copolymers of acrylic acid and acrylamide ("sulfonated copolymers") are used in the treatment of industrial cooling water to prevent corrosion and mineral deposits (scale). The active sulfonated copolymers typically remove dissolved minerals from the cooling water by complexing with the mineral. Over time the complexation sites of the sulfonated copolymer molecules become saturated and the copolymer molecules become inactive, i.e., unable to remove any additional minerals from the cooling water.

To prevent corrosion and scale damage to machinery used for water based industrial cooling systems, as the polymers are inactivated they must be removed and replaced by active sulfonated copolymer. Thus, active sulfonated copolymer must be continually fed into the cooling water to replace the inactive sulfonated copolymer. Maintaining the proper feed level for the active sulfonated copolymer is essential for optimum performance of the water system. An improper feed rate can lead to serious problems. For example, insufficient active sulfonated copolymer can result in the water treatment being overwhelmed by dissolved minerals, thereby causing severe corrosion or scale deposit. On the other hand, maintaining too high a level of the active polymer is very expensive and is an inefficient method for treating industrial cooling water. It is important, therefore, to monitor polymer levels to achieve proper balance of polymers in the containers.

Another class of water-soluble, vinyl polymers, acrylate homopolymers ("polyacrylates"), are used in the treatment of industrial boiler water to prevent corrosion and mineral deposits (scale). These polymers do not have side chains, in contrast to sulfonated copolymers. A polyacrylate commonly removes dissolved minerals from the boiler water by complexing with the mineral. As with sulfonated copolymers, the complexation sites of the polyacrylate become saturated over time, inactivating the molecule and precluding removal thereby of additional minerals from the boiler water.

To prevent corrosion and scale damage to machinery, inactivated polyacrylate polymers must be removed and replaced by active polyacrylate, necessitating a continual input of active polyacrylate into the boiler water. Because maintaining the proper feed level of polyacrylate thus is essential for optimum performance, an improper feed rate can lead to serious problems, much the same as with sulfonated copolymers (see above). By the same token, therefore, it is important to monitor polymer levels to achieve proper balance of polymers in the boilers.

The several methods available conventionally for the determination of polymer concentration in these contexts suffer from lack of specificity or poor sensitivity. For example, the older methods for detecting polyacrylates or sulfonated copolymers include colloid titration with PVSK, complexation with hyamine 1622, or reaction of excess magnesium with chrome azurol S. The above tests detect any polyanionic material and have a detection threshold of only about 50 ppm polymer, which is inadequate to monitor polymers used for preventing mineral deposits.

Presently, the amount of polymers in treated industrial water systems such as polyacrylate in an industrial boiler water system or sulfonated copolymers in industrial cooling systems cannot be inexpensively and rapidly determined. Therefore, monoclonal antibodies were developed which are directed toward polymers such as polyacrylate and sulfonated copolymers in order to detect the polymers and to monitor their concentration to optimize treatment.

SUMMARY OF THE INVENTION

One aspect of the present invention is directed to a monoclonal antibody having an affinity to a polymer, in particular a water-soluble, vinyl polymer such as a sulfonated copolymer of acrylic acid and acrylamide or a polyacrylate. When used in some detection formats, the monoclonal antibodies of the present invention have an absolute specificity for the polymers and a lower limit of detection in the femtogram per ml range. These high specificities and ability to detect small amounts of polymer in a sample, represent a significant improvement over assays for polymers in industrial water samples. Moreover, the methods are derived from a completely different concept than previously known in the field of industrial water quality management, a concept that employs monoclonal antibodies.

The invention is directed to novel assays for the detection of chemicals, particularly polymers, in particular water soluble, vinyl polymers, such as polyacrylate and copolymers of polyacrylic acid and acrylamide, which are employed to prevent corrosion and mineral deposits in the containers of water used for industrial purposes, assays which are suitable for use in conditions which exist in boiler water and in industrial cooling water. Different polymers are used for the different applications depending on the nature of the mineral deposits in the container to be treated.

Testing of the immunoassay under conditions reminiscent of those associated with industrial water treatment with corrosion preventive chemicals show the successful use of monoclonal antibodies to monitor such treatment.

The monoclonal antibodies of the invention are produced by hybridoma cell lines. Preferred hybridoma cell lines suitable for practice of the invention include hybridoma cell line 6E2-H1-G4 (ATCC No. HB 11015) which is used to detect both sulfonated and non-sulfonated polymers, but with different binding affinities; 6D12-H9-G3 (ATCC No. HB 11016) which is preferred for detecting sulfonated copolymers. Another preferred hybridoma cell line of the invention is hybridoma cell line 4F12-C12, which is used for detecting non-sulfonated polymers. A still further preferred hybridoma cell line is 4B1-H6-E10.

Another aspect of the invention is directed to a method of manufacturing a monoclonal antibody having an affinity to a water soluble, vinyl polymer useful in preventing corrosion in industrial water systems. The inventive method includes the steps of: (a) immunizing a mammal with the polymer attached to a carrier protein; (b) preparing a hybridoma cell producing the monoclonal antibody from cells removed from the immunized mammal; (c) cloning the hybridoma cell to produce a hybridoma cell line; and (d) extracting the monoclonal antibody from the hybridoma cell line.

When sulfonated copolymers of acrylic acid and acrylamide were used for immunizing, various hybridomas were obtained, in accordance with the present invention. These are a source of monoclonal antibodies, which complex with the polymer and are suitable for use in its detection. By means of the methods disclosed herein, multiple hybridomas were produced that were suitable for use in the present invention. Therefore, it is to be expected that others can be produced readily, using these methods. Resulting antibodies vary in binding profiles and specificity, however. For example, a preferred hybridoma cell line for this purpose is hybridoma cell line 6E2-H1-G4. Accordingly, in other preferred embodiments of the invention, the hybridoma cell line is hybridoma cell line 4F12-C12 or 4B1-H6-E10.

A further aspect of the present invention is directed to a process for the determination of the presence or concentration of the polymers in an industrial water sample. The inventive process includes the step of incubating a sample of the fluid containing the polymer with a monoclonal antibody having an affinity for the polymer. In some assays the monoclonal antibody is bound to a solid carrier.

Assays employing the monoclonal antibodies of the present invention have been tested in simulated field specimens and shown to have high sensitivity and specificity. The necessity of a specific antigen-antibody complex component of the assay to provide results, the ability of the assay to differentiate among polymer types depending on the monoclonal antibody used, and the ability of the assay to quantitate the amount of specific polymer detected, are aspects of the invention.

The detection of an antibody-antigen complex may be achieved by use of an enzyme-linked immunoassay, including one wherein the antibody is attached to a solid support such as a microtiter plate or a bead. Sandwich, competition and indirect immunoassays are suitable. In other embodiments, solid supports are not needed, for example when using precipitation reactions in a gel, e.g. the Ouchtolony method.

Another aspect of the present invention is a kit employing monoclonal antibodies to monitor polymers used to treat industrial water. The kit contains a monoclonal antibody for the determination of the presence or concentration of the polymers in an industrial water sample. The inventive process includes the step of incubating a sample of the fluid containing the polymer with a monoclonal antibody having an affinity for the polymer detecting the formation of an antigen antibody complex and quantitating the amount of antigen present in the sample. In some assays the monoclonal antibody is bound to a solid carrier.

The monoclonal antibody is preferably one that is specific for the antigen. The kit provides an environment in which an antigen-antibody complex occurs between a sample of water to be tested, and the antibody provided in the kit. An example of a suitable environment is a plastic tube coated with the antibody into which the fluid sample to be tested is poured.

An observable reaction indicative of the formation of an antigen antibody complex is provided in the kit. This reaction includes a colorimetric reaction. If the complex forms on beads, it may be detected by attachment of a small colored bead which is small enough to pass through a provided filter, with a larger uncolored bead when the complex forms, resulting in bead combinations that will not pass through the filter and will be detected by color on the filter.

| Figure Legend: | Capture Ab | Detection Ab |
| --- | --- | --- |
| Column 1 | anti-Prism | anti-Prism |
| Column 2 | anti-Prism | anti-EDC-Ammonia |
| Column 3 | anti-EDC-Ammonia | anti-Prism |

(PRISM ® is a Nalco trademark for a sulfonated copolymer of acrylic acid and acrylamide)

Figure 12:
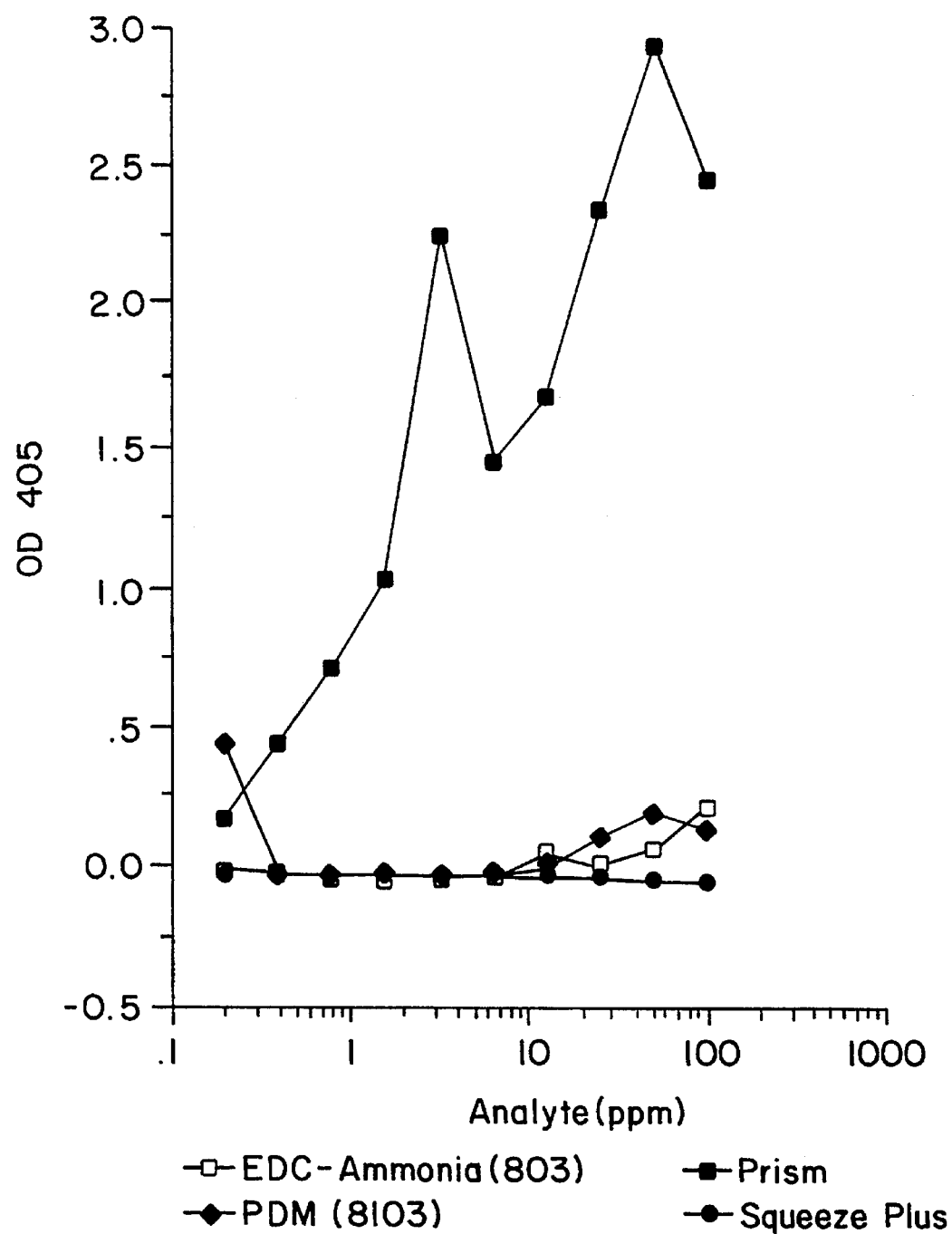

FIG. 12 shows that when a monoclonal antibody for PRISM is present in the micotiter plate sandwich assay only PRISM® shows quantitative detection. In the cross-reactivity profile shown, the controls (EDC-ammonia, Polydadmac, and Squeeze Plus, other polymers available from Nalco) were not detected.

Figure 13:
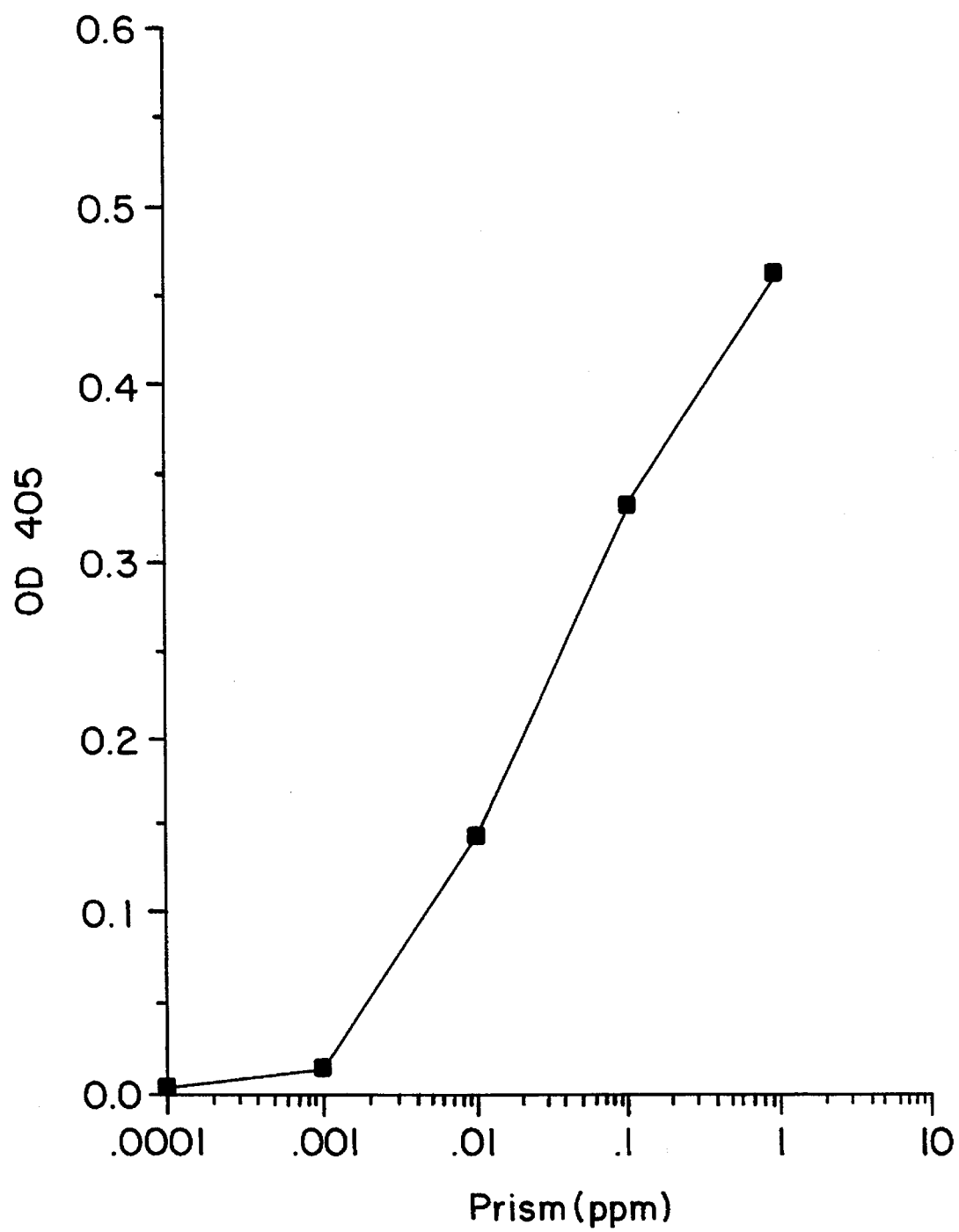

FIG. 13 demonstates the appearance of a standard curve used to detect even small amounts of PRISM® using a specific monoclonal assay to PRISM®.

DETAILED DESCRIPTION OF PREFERRED EMBODIMENTS

Hybridoma cell lines producing monoclonal antibodies having an affinity for water soluble, vinyl polymers have been invented. The monoclonal antibodies of the invention bind to such polymers with varying degrees of specificity, and if cross-reactive, with different binding affinities. By using two different assay formats, it has been determined that these monoclonal antibodies recognize and differentiate among polymers, in particular water soluble, vinyl polymers at concentrations ranging from zero to a few hundred parts per million. Examples described herein demonstrate the feasibility of using the monoclonal antibodies of the invention to determine the presence or concentration of these polymers in fluids, such as water samples from industrial boilers and industrial water cooling systems.

It was unexpected that monoclonal antibodies would successfully be developed to water soluble, vinyl polymers such as sulfonated copolymers or polyacrylate, and that their use would have so many advantages. Advantages of antibody assays in overcoming limitations of current methods used to monitor chemical treatment of industrial boiler water include high specificity and sensitivity, low cost and ease of use.

Monoclonal antibodies were not previously employed by those involved in industrial water quality testing. Use of monoclonal antibody assays for water quality monitoring and treatment efficacy was not known in the art. Therefore, those interested in monitoring treatment of industrial boiler water, would not have expected to employ monoclonal antibodies to monitor treatment. Those working in this field would have no reason to anticipate success in producing monoclonal antibodies and using them to assay water quality based on polymer content.

Considering the technical feasibility of making an antibody that is specific to a chemical, it was not expected that antibodies could be made to polyacrylate because of the structure and features of the polymers.

The molecular structure of polymers of the present invention would not have led those of skill in the art to expect polyacrylate to be sufficiently antigenic to form the basis for a useful immunoassay. Also, uses of monoclonal antibodies for the purpose of the present invention were not endemic to the field of industrial water quality testing before the present invention was made.

Monoclonal antibodies are not so well known that making and using them is routine in every case. Awareness of monoclonal antibodies varies among research areas. What may be well-known in clinical diagnosis, for example, is not necessarily routine in other areas of endeavor. Use of monoclonal antibodies is unprecedented in the field of industrial water treatment. Indeed, using monoclonal antibodies for monitoring chemical treatment of industrial water is a new concept in the field, and its success was not reasonably predictable.

Knowledge of the molecular structure of polyacrylate, the chemical used to treat industrial boiler water, did not lead to an expectation of success in producing monoclonal antibodies for an industrial immunoassay. Table 1 shows that the position of acrylate polymers in three critical classes of features used to predict a possible immune response suggests that such polymers would generate a poor immune response. Thus, polymers of the type used in the present invention share key features with other materials that are known to be poor immunogens.

Acrylate polymers were expected to be poor antigens. This is because their molecular weight and lack of linear sequences, which are required for antibody binding, led to the expectation they would produce, at best, low affinity antibodies which would not be useful for an immunoassay. Although the expediency of conjugating the polymers to a protein known to be strongly antigenic proved ultimately to be a successful strategy for applicant, this approach was not reasonably certain of success, in light of what was known in the relevant art at the time.

Structural features of a chemical of interest may be compared to similar molecules to predict success in stimulating an immune response. Comparison of antigens of the present invention with other molecules, on the basis of three critical classes of features used to predict a possible immune response, did not suggest success in producing monoclonal antibodies directed to the antigens (see Table 1). Structural complexity, as measured by the number of monomers in the polymers, is important to the host animals's recognition of a polymer as an antigen. Because acrylate polymers have only two monomers, the expectation was for poor immune response. On the basis of all these comparisons, actually producing an antibody to polyacrylate was surprising because the copolymers shares key features with other materials that are poor immunogens.

TABLE 1

Prediction of Immune Response from Three Molecular Features:

| Feature | Immune Response | Potential or Known Antigen |
| --- | --- | --- |
| 20 monomers | excellent | protein |
| 5–10 monomers | fair | bacterial capsules |
| 4 monomers | poor | nucleic acids |
| 2 monomers | expected very poor | acrylate polymers |
| 1 monomer | extremely poor | starch, cellulose |
| high order | excellent | protein |
| moderate order | fair | bacterial capsules |
| slight order | poor | nucleic acids |
| random order | expected very poor | acrylate polymers |
| mixed charge | excellent | only protein |
| only ⊕ | poor | p-lysine |
| only ⊖ | poor | p-alanine |
| only ⊖ | expected poor | acrylate polymers |

Handbook of Experimental Immunology, Number 1, "Immunochemistry" (D. M. Weir, ed.) 4th edition (1986), Blackwell Scientific Publications.

Table 1 would not have engendered an expectation that the polymers of the present invention would be antigenic. In practice, the polymers were poor antigens. The test animals did not respond immunologically to the polymers, even after multiple injections. In fact, multiple injections proved unexpectedly unsuitable, because cross-reactivity developed after 2–4 immunizations. This was unexpected because generally, when encountering low titres of antibody, multiple injections, for example 7–8, will solve the problem. In search of a solution to the low titres produced by the polymers of the present invention, only 2–3 injections were preferred, and another approach was tried. The polymers were chemically conjugated to a protein known to be strongly antigenic. The concept was that the test animal's immune system may react to the antigen protein, and further that some of the antibodies may thereby react with the attached (conjugated) polymer. However, such conjugation does not predictably achieve the desired result, and in any case, would not be expected to solve the cross-reactivity problem. Therefore, success was not expected.

Fortunately, the minimum injection-conjugation approach was successful. Mice responded by producing antibodies to the polymers of the present invention. These antibodies were the first known to be produced that were specific for these synthetic polymers. The specificity was unexpected in view of early cross-reactivity. The mice producing these antibodies were used as the basis for production of hybridomas and monoclonal antibodies by standard techniques.

Monoclonal antibodies were tested for their ability to react with the specific polymers under conditions of scale formation as found in industrial boiler water or cooling water systems. The tests showed a clear and positive correlation between the expected amount of free polymer, the free polymer measured by the traditional method of precipitation, and the free polymer measured by an immunological test which was a function of the monoclonal antibodies (See Example 14).

In these tests, the starting material was a warm solution of calcium, magnesium, phosphate and polymer at a low pH. The gradual addition of sodium hydroxide raised the pH and caused the formation of insoluble calcium and magnesium salts. If no polymer is present, mineral precipitation occurs rapidly, and large calcium/magnesium phosphate aggregates form. If an effective polymer is present, mineral precipitation is retarded or completely eliminated. The action of retarding mineral precipitation consumes the polymer.

By experience and industry convention, a mineral particle is considered dispersed or stabilized if it is less than about 0.05 μm in diameter. See "Influence of Mechanistic Studies on the Development of New Cooling Water Programs," *Corrosion '89*, Paper 175, National Association of Corrosion Engineers (Houston, Tex. 1989). This means that material passing through a filter of 0.05 μm pore size is considered free polymer. Conversely, polymer retained by the filter is embedded in mineral aggregates and has been consumed.

Testing by the standard non-specific precipitation assay showed polymer in the filtered fluid decreased as expected during sodium hydroxide addition. Testing of the same samples with an immunodiffusion assay based on the present invention showed a similar decrease in polymer concentration as pH increased and polymer was consumed by mineral scale formation. The immunodiffusion assay is inherently superior to the traditional assay because of the specificity of the antibody of the particular polymer with which it reacts.

Figure 11:
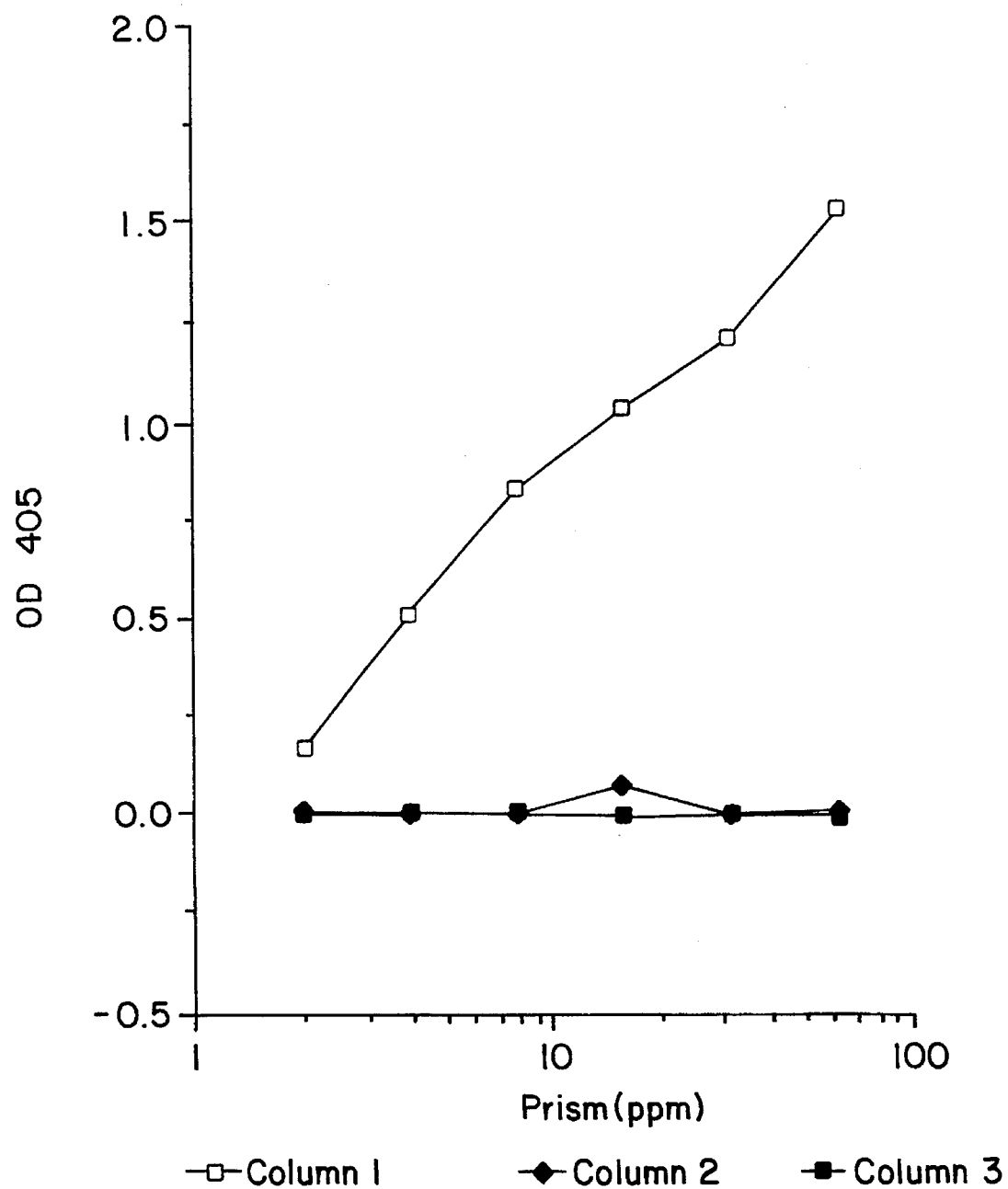
FIG. 11 illustrates that correct components are needed for the capture antibody and the detection antibody to quantitatively distinguish polymers spiked in a water composition tested for the presence of the antigen (polymer) using a microtiter sandwich assay; this graph shows a standard curve for PRISM( a sulfonated copolymer sold by Nalco for use in industrial water treatment) obtained using a microtiter plate sandwich assay. Control experiments were run in which an anti-EDC-Ammonia antibody (instead of the anti-PRISM antibody) was used for capture or detection. PRISM was not detected in the control experiments which demonstates the specific nature of the assay.

FIGS. 11–13 indicate the success of the methods in samples of water spiked with the polymers and appropriate controls as indicated in the figures.

The antibody response of a particular animal is not infinite, but restricted genetically, and thus the number and kinds of antibodies possible is also limited. In addition, the binding of antigen and antibody is governed by well defined chemical laws which allow one skilled in the art to make predictions regarding the potential success of making antibodies to any given antigen, but which also impose absolute limitations on the types of antibodies that can be elicited.

Highly inbred strains of mice, such as those used to make MAbs, are genetically restricted in their capacity to make antibodies to many polymeric antigens (for example, polysaccharides) and especially small polymers comprised of low number of monomeric units, such as the polymers of the present invention. Given the often profound genetic restriction of mice to make antibodies to many polymers, one skilled in the art would not predict the successful isolation of useful MAbs from mice immunized with such antigens.

For a useful immunoassay, it is not enough for an antibody to be produced, but in addition, the antibody must possess certain characteristics. The utility of any antibody is determined by its sensitivity and specificity for a given antigen. The sensitivity and specificity of an antibody are determined by the chemical interactions between the antibody and the antigen. The chemical groups, the linear sequence of monomeric units and the three-dimensional, spatial conformation of a polymeric antigen all contribute to the strength of binding between antigen and antibody.

The types of chemical bonds known to contribute to binding between antigen and antibody include; hydrophobic, Vander Waals, hydrogen bonding and ionic. It is well established in the art that the binding of antigen by antibody is a result of the formation of multiple non-covalent bonds between the two. The greater the number of bonds the greater the strength of binding. Hydrophobic bonds play a particularly important role in antibody binding and may contribute up to half of the total strength of the antigen-antibody bond (M. Steward, 1989. In "Immunology" et. by, I. Roitt, J. B. Lippincott, Philadelphia, p. 7.1). It is also well established in the art that polymers having a variety of different chemical groups are better antigens than those having only a single type of group for bonding. Indeed, polymers having only ionic groups available for binding are poor antigens. Further, antigens having only one type of ionic group (i.e., positive or negative) are very poor antigens (M. Sela, 1978, In, "Handbook of Experimental Immunology," ed. by, D. M. Weir, Blackwell, Oxford, p. 1.2). For an antibody to be useful in the instant invention it must be both sensitive and specific for the detection of polyacrylate.

The sensitivity of an immunoassay ultimately depends on the 'strength' of binding of antigen by antibody. In general, the stronger the antibody binds antigen, the greater the sensitivity of the immunoassay. The 'strength' by which an antibody binds an antigen is referred to as 'affinity' which can be measured and expressed as an affinity constant.

Useful, commercial diagnostic immunoassays generally require the use of antibodies having affinities of at least $10^8$ $M^{-1}$, preferably of $10^9$ $M^{-1}$ (U.S. Pat. No. 4,486,530). The affinity for polyacrylate, for example, would be expected to be low based on its size and structure, therefore, would be unlikely to work for the goals of the present invention.

The structure of polyacrylate is not suggestive that polyacrylate would have a good antigen binding site. Recognition and binding of antigen by most antibodies is highly dependent on the three-dimensional or spatial structure of the antigen (Berzofsky et al., 1989. In "Fundamental Immunology," ed. by, W. E. Paul, Raven Press, New York, P. 177). It is well established in the art that most antibodies elicited in response to injection of a given antigen only bind that antigen when it exists in a very specific spatial configuration and does not bind the same molecule when it is conformationally denatured. Each polymer molecule within a preparation of a random copolymer has a unique linear sequence of monomer units and thus would be expected to have different conformations. In fact, such polymers are not considered to adopt specific conformations. From this it would not be expected by one skilled in the art that production of MAbs which recognize conformational determinants on all the polyacrylate molecules, would be possible.

The size of an antibody combining site is sufficient to bind multiple monomeric units within a polymeric structure. There are many references in the art which define the size of an antibody binding site to be approximately 4–6 amino acid residues for protein antigens and as many as 10 monosaccharide units for polysaccharide antigens. Many antibodies are known to recognize very specific linear sequences of monomeric units within polymers. Substitution of a single amino acid within a protein sequence or a monosaccharide within a polysaccharide can completely obliterate antibody binding.

Random copolymers composed of two monomer units such as those of the instant invention do not possess specific linear sequences. Indeed, every polymer molecule within a population of molecules has a unique sequence. The reactivity of an antibody elicited to a specific linear sequence of monomers on one random copolymer molecule with other molecules in the same population depends on the presence of that sequence on all the other molecules in the population. The statistical probability that such a sequence exists on all, or even any, of the random copolymer molecules within a population decrease with decreasing polymer molecular weight.

Covalent conjugation of polyacrylate to a hapten would not be expected to change it from a poor to a good antigen. The overall effect of conjugation of a hapten to an immunogenic protein carrier is to increase the level of antibody production and alter the effector function of the antibody within the body of the animal. Conjugation of a poorly antigenic molecule to an immunogenic carrier does not alter the absolute fundamental nature of the chemical interaction between antibody and antigen. The same identical chemical bonds which determine the strength of antigen-antibody binding, sensitivity, specificity and ultimate utility of an antibody are unchanged as a result of conjugation to protein. Because the chemical nature of the polyacrylate of the instant invention is the same after conjugation as before, one skilled in the art would predict that covalent conjugation would only serve to increase production of the same low affinity, low specificity antibodies previously contemplated.

The mechanism by which this occurs is also well established in the art (Berzofsky et al., supra). Cells within the immune system of mammals known as T-cells recognize the protein component of the hapten-protein conjugate and bind to it. Once bound they become activated and secrete a variety of molecules that act to 'help' antibody production by antibody producing B-cells. This 'help' causes the antibody producing B-cells to increase their rate of antibody production, undergo cell division and cause antibody isotype switching. The part of an antibody molecule which is not involved in antibody binding to antigen determines the isotype of the antibody. The isotype of the antibody determines the effector function the antibody will have in the body of the animal. Isotype-switching as a result of T-cell help does not effect antibody-antigen binding.

Hybridoma cell lines producing monoclonal antibodies having an affinity for sulfonated copolymers of acrylic acid and acrylamide (SCP) have been invented and are herein described and claimed. The monoclonal antibodies of the invention bind to SCP with varying degrees of specificity. By using two different assay formats, it has been conclusively proven that these monoclonal antibodies can recognize SCP at concentrations ranging from zero to a few hundred parts per million. Examples described herein demonstrate the feasibility of using the monoclonal antibodies of the invention to determine the presence or concentration of SCP in fluids, such as water samples from industrial cooling water towers.

Accordingly to one embodiment of the invention, a monoclonal antibody having an affinity to sulfonated copolymer is used in an Enzyme Linked Immunosorbent Assay (ELISA) for determining the concentration of SCP in a fluid sample. ELISA formats using the monoclonal antibodies of the invention are preferred for measuring the concentration of SCP in fluid samples. Three preferred immunoassay strategies are sandwich ELISA, competition ELISA and indirect ELISA. Although several antibodies described herein are useful in assaying SCP in a fluid sample, the two most preferred monoclonal antibodies are those produced by hybridoma cell lines 6E2-H1-G4 and 6D12-H9-G3 since these two clones have shown the greatest anti-SCP specificity in indirect ELISAS.

According to one preferred embodiment of the invention a sandwich ELISA will be used for measuring the concentration of SCP. Preferably, purified anti-SCP antibody will be used as a capture antibody. The antibody will be adsorbed to wells of 96-well microtiter plates. Test samples containing SCP will be added and allowed to bind to the capture antibody. In the next step, enzyme labelled anti-SCP antibody will be added and allowed to bind to the exposed antigenic sites on the SCP molecules captured by the coating antibody. The amount of enzyme labelled antibody retained after washing would therefore correlate directly with the amount of SCP in the sample. The level of enzyme label bound in each well will be quantitated by incubation with a chromogenic enzyme substrate and measurement of the resulting color change. A standard curve will be generated using known concentrations of SCP polymer. This approach has the advantage of higher sensitivity normally associated with sandwich ELISAS.

In another preferred embodiment, a competition ELISA is used to measure the SCP for a fluid sample. Accordingly to this embodiment, purified anti-SCP antibody will be adsorbed onto wells of 96-well microtiter plates. Test samples containing SCP will be added to the plates with known quantities of enzyme-labelled SCP polymer. The amount of enzyme-labelled SCP retained after washing will be inversely proportional to the amount of SCP originally present in the test samples. The amount of enzyme present will be measured by the addition of a suitable chromogenic substrate. Standard curves will be generated using known quantities of SCP. This particular format has the advantage of being essentially a one-step assay with only one incubation period.

According to still another embodiment of the invention, indirect ELISA assay is used to measure the concentration of SCP in a fluid. According to the embodiment, known quantities of Bovine Serum Albumin (BSA-SCP) conjugate will be adsorbed to replicate wells of 96 well microtiter plates. Next, various dilutions of the anti-SCP monoclonal antibody will be allowed to bind to the immobilized SCP. Enzyme-labelled goat anti-mouse Ig will be added next and allowed to bind to the primary antibody. A chromogenic substrate will then be added which will be converted to a colored product by the bound enzyme. The resultant color change will be quantified by measuring the absorbance (optical density) at 492 nm. The amount of color change will be proportional to the amount of enzyme-labelled antibody retained and thus will correlate directly with the amount of anti-SCP antibody which was able to initially bind to the immobilized SCP. The results of this experiment will yield the optimal concentration of anti-SCP antibody to use in the assay.

Having defined the appropriate concentration of antibody for an indirect ELISA, inhibition of binding between the monoclonal antibody and the SCP-coated microtiter plates by SCP present in solution will be determined. The monoclonal anti-SCP primary antibody will be incubated with various concentrations of SCP before being added to the SCP-coated microtiter plates. A standard curve will then be prepared by plotting the percentage inhibition as a function of free SCP concentration. This will be carried out for each fixed quantity of immobilized SCP and the primary antibody. This assay format will be suitable if this standard curve shows a steep dose-response at the concentrations that are relevant to those which occur in cooling water samples. It has the advantage of not requiring any additional purification or modification of the anti-SCP monoclonal antibody.

Any of the assays discussed above could be further developed and refined using other solid support systems such as coated tubes and polymer membranes. However, the sandwich ELISA or the competition ELISA formats are preferred since they could be designed as a "dipstick" assay. Nevertheless, any of the above assay formats are intended to be used with the monoclonal antibodies of the present invention to measure the concentration of SCP in a fluid sample.

According to one embodiment of the invention, a monoclonal antibody having an affinity to polyacrylate is used in an Enzyme Linked Immunosorbent Assay (ELISA) for determining the concentration of polyacrylate in a fluid sample. ELISA formats using the monoclonal antibodies of the invention are preferred for measuring the concentration of polyacrylate in fluid samples. Three preferred immunoassay strategies are sandwich ELISA, competition ELISA and indirect ELISA. Although several antibodies described herein are useful in assaying polyacrylate in a fluid sample, the two most preferred monoclonal antibodies are those produced by hybridoma cell lines 6E2-H1-G4 (deposited as ATCC accession number HB 11015) and 4F12-C12 because these two clones have shown the greatest anti-polyacrylate specificity in indirect ELISAS.

According to one preferred embodiment of the invention, a sandwich ELISA is used for measuring the concentration of polyacrylate. Preferably, purified anti-polyacrylate antibody is used as a capture antibody. The antibody is adsorbed to wells of 96-well microtiter plates. Test samples containing polyacrylate is added and allowed to bind to the capture antibody. In the next step, enzyme-labelled anti-polyacrylate antibody will be added and allowed to bind to the exposed antigenic sites on the polyacrylate molecules captured by the coating antibody. The amount of enzyme labelled antibody retained after washing would therefore correlate directly with the amount of polyacrylate in the sample. The level of enzyme label bound in each well will be quantitated by incubation with a chromogenic enzyme substrate and measurement of the resulting color change. A standard curve is generated using known concentrations of polyacrylate polymer. This approach has the advantage of higher sensitivity normally associated with sandwich ELISAs.

In another preferred embodiment, a competition ELISA is used to measure the polyacrylate for a fluid sample. According to this embodiment, purified anti-polyacrylate antibody will be adsorbed onto wells of 96-well microtiter plates. Test samples containing polyacrylate are added to the plates along with known quantities of enzyme-labelled polyacrylate polymer. The amount of enzyme-labelled polyacrylate retained after washing is inversely proportional to the amount of polyacrylate originally present in the test samples. The amount of enzyme present is measured by the addition of a suitable chromogenic substrate. Standard curves are generated using known quantities of polyacrylate. This particular format has the advantage of being essentially a one-step assay with only one incubation period.

According to a still further embodiment of the invention, indirect ELISA assay is utilized to measure the concentration of polyacrylate in a fluid. According to the embodiment, known quantities of Bovine Serum Albumin (BSA-polyacrylate) conjugate are absorbed to replicate wells of 96 well microtiter plates. Next, various dilutions of the anti-polyacrylate monoclonal antibody will be allowed to bind to the immobilized polyacrylate. Enzyme-labelled goat anti-mouse Ig are added next and allowed to bind to the primary antibody. A chromogenic substrate is then added which will be converted to a colored product by the bound enzyme. The resultant color change is quantified by measuring the absorbance (optical density) at 492 nm. The amount of color change is proportional to the amount of enzyme-labelled antibody retained and thus correlates directly with the amount of anti-polyacrylate antibody which is able to initially bind to the immobilized polyacrylate. The results of this experiment yield the optimal concentration of anti-polyacrylate antibody to use in the assay.

With the appropriate concentration of antibody defined for an indirect ELISA, inhibition of binding between the monoclonal antibody and the polyacrylate-coated microtiter plates by polyacrylate present in solution is determined. The monoclonal anti-polyacrylate primary antibody is incubated with various concentrations of polyacrylate before being added to the polyacrylate-coated microtiter plates. A standard curve is then prepared by plotting the percentage inhibition as a function of free polyacrylate concentration. This is carried out for each fixed quantity of immobilized polyacrylate and the primary antibody. This assay format is suitable if this standard curve shows a steep dose-response at the concentrations that are relevant to those which occur in industrial water samples. It has the advantage of not requiring any additional purification or modification of the anti-polyacrylate monoclonal antibody.

Any of the assays discussed above could be further developed and refined using other solid support systems such as coated tubes and polymer membranes. However, the sandwich ELISA or the competition ELISA formats are preferred since they could be designed as a "dipstick" assay. Nevertheless, any of the above assay formats are intended to be used with the monoclonal antibodies of the present invention to measure the concentration of polyacrylate in a fluid sample.

The following examples are presented to describe preferred embodiments and utilities of the invention and are not meant to limit the invention unless otherwise stated in the claims appended hereto.

EXAMPLE 1

Antigen Synthesis: Sulfonated Copolymers of Polyacrylic Acid and Acrylamide

The antigens used to immunize mammals were prepared as follows:

Twenty mg of the polymer was first derivatized with the coupling agent, 1-ethyl 3(3'-dimethylamino-propyl) carbodiimide (EDC) at a pH of 5.0. After a 15 minute incubation at room temperature, 15 mg of Keyhole Limpet Hemocyanin (KLH) or 10 mg of Bovine Serum Albumin (BSA) was added and allowed to react at pH 7.0 for 4 hours, also at room temperature. Small molecular weight side products were removed by overnight dialysis at 4° C.

Both sulfonated (SCP) and non-sulfonated (CP) forms of the acrylate-acrylamide copolymers were tested. The sulfonated copolymer was obtained from Nalco Chemical Company under the tradename designation PRISM™. The non-sulfonated copolymer was also obtained from Nalco Chemical Company. High and low molecular weight fragments were tested for both forms. Exact molecular weights of the copolymers were 6.6 kD and 23 kD for the non-sulfonated forms and 7.4 kD and 26 kD for the sulfonated forms. The smaller molecular weight copolymers, both sulfonated and non-sulfonated, were conjugated through carboxylic acid residues on the copolymers to amino groups on the carrier proteins KLH and BSA using the coupling agent EDC as described above. Gel electrophoresis of the BSA conjugate indicated successful conjugation with approximately one to four copolymer molecules conjugated per molecule of BSA. The KLH conjugates were too heterogeneous and less well defined to be meaningfully analyzed by electrophoresis.

EXAMPLE 2

Antigen Synthesis: Polyacrylate

The antigens were prepared as follows:

Ten mg of the polyacrylate (35K) having a molecular weight of about 35KD was obtained from the Nalco Chemical Company. The polyacrylate was first derivatized with the coupling agent, 1-ethyl 3(3'-dimethylamino-propyl) carbodiimide (EDC) at a pH of 5.0. After a 15 minute incubation at room temperature, 10 mg of Bovine Serum Albumin (BSA) was added and allowed to react at pH 7.0 for 4 hours, also at room temperature. Small molecular weight side products were removed by overnight dialysis at 4° C. Gel electrophoresis of the BSA conjugate indicated successful conjugation with approximately one to four polymer molecules conjugated per molecule of BSA.

EXAMPLE 3

Utility of SCP-BSA Conjugate in Indirect ELISA Screening

The BSA conjugates of the lower molecular weight copolymers of SCP were tested for adsorption onto microtiter plates by performing an indirect ELISA using rabbit anti-BSA antiserum. Plates were coated with the conjugates at a concentration of 0.01 mg/ml (0.5 µg/well) in phosphate-buffered saline, pH 7.2 (PBS). Unoccupied sites on the plates were blocked with a 5% solution of non-fat milk in PBS. Dilutions of rabbit anti-BSA antiserum were incubated with the plate. Horseradish peroxidase (HRP) labelled goat anti-rabbit antibody was then allowed to bind to the primary anti-BSA antibody. The bound enzyme (HRP) was then quantitated with a chromogenic substrate. These assays were performed in duplicate, the results are tabulated in Table 2. These results clearly indicate that the BSA conjugates bound strongly to the ELISA plates, thus confirming the utility of these conjugates for the screening of anti-SCP antibodies in an indirect ELISA format.

TABLE 2

| | Indirect ELISA with Rb anti-BSA sera | | |
|---|---|---|---|
| Set | Antigen | $OD_{1/2max}$ | Titer value |
| #1 | SCP-BSA | 0.96 | 1:9000 |
| | CP-BSA | 0.94 | 1:7100 |
| | BSA | 0.87 | 1:14,000 |
| | No Ag | 0.31 | 1:50 |
| #2 | SCP-BSA | 0.94 | 1:9000 |
| | CP-BSA | 0.92 | 1:7700 |
| | BSA | 0.86 | 1:13,000 |
| | No Ag | 0.36 | <1:50 |

EXAMPLE 4

Utility of Polyacrylate-BSA Conjugate in Indirect ELISA Screening

The BSA conjugates of the polyacrylate were tested for adsorption onto microtiter plates by performing an indirect ELISA using rabbit anti-BSA antiserum. Plates were coated with the conjugates at a concentration of 0.01 mg/ml (0.5 µg/well) in phosphate-buffered saline, pH 7.2 (PBS). Unoccupied sites on the plates were blocked with a 5% solution of non-fat milk in PBS. Dilutions of rabbit anti-BSA antiserum were incubated with the plate. Horseradish peroxidase (HRP) labelled goat anti-rabbit antibody was then allowed to bind to the primary anti-BSA antibody. The bound enzyme (HRP) was then quantitated with a chromogenic substrate. These assays were performed in duplicate. The results of the assay are summarized in Table 3. These results clearly indicate that the BSA-polyacrylate conjugates bound strongly to the ELISA plates, thus confirming the utility of these conjugates for the screening of antipolyacrylate antibodies in an indirect ELISA format.

TABLE 3

| Indirect ELISA with Rb anti-BSA sera | | | |
|---|---|---|---|
| Set | Antigen | $OD_{1/2max}$ | Titer value |
| #1 | 35K-BSA | 0.94 | 1:7100 |
|  | BSA | 0.87 | 1:14,000 |
|  | No Ag | 0.31 | 1:50 |
| #2 | 35K-BSA | 0.92 | 1:7700 |
|  | BSA | 0.86 | 1:13,000 |
|  | No Ag | 0.36 | <1:50 |

EXAMPLE 5

Immunization

Immunization of four groups (A–D) of female Balb/c mice, five mice per group, approximately 9–12 weeks of age, was performed. Groups A and B were boosted weekly with 100 μg of SCP-KLH immunogen per mouse administered via intraperitoneal injection. Group A received immunogen emulsified in Freund's adjuvant, Group B received immunogen emulsified in Ribi's adjuvant. Groups C and D received weekly immunizations of 100 μg of unconjugated SCP immunogen per mouse emulsified in Freund's adjuvant or Ribi's adjuvant respectively. Mice were bled periodically and each serum sample was evaluated by indirect ELISA against SCP-BSA and CP-BSA. Antibody titer values were determined from the ELISA results; antibody titer being defined as the dilution of the sample sera which yields an optical density that is one-half of the maximum signal obtained ($OD_{1/2}$max) in an indirect ELISA. Table 2 presents the titer results obtained for all four groups of animals.

EXAMPLE 6

Fusion

Mice with elevated antibody titer against SCP-BSA were sacrificed and the splenocytes were isolated and fused with Hypoxanthine Guanidine Phosphoribosyl Transferase (HGPRT) deficient SP2/0 plasmacytoma cells utilizing polyethylene glycol (PEG) as the fusing agent. Fusion #1 was performed with the two mice from Group B which had titers of 1:11,000 and 1:14,000, respectively, against SCP-BSA. Their corresponding titer values against CP-BSA were 1:4700 and 1:6700. Fusion #2 was performed using two mice from Group E (an additional group of mice which was subsequently started) with anti-SCP-BSA titer values of 1:2600 and 1:2900 respectively. Their corresponding titer values against CP-BSA were 1:1000 and 1:920. The fused cells were plated into 96-well tissue culture plates and the resultant hybridomas were identified by selection in Hypoxanthine Aminopterin Thymidine (HAT) medium. The hybridoma cell lines developed which produced anti-SCP monoclonal antibodies were 6E2-H1-G4, 6D12-H9-G3, 6C8-F1-F9, 4D4-C9-F6, 4B1-H6E10 and 4F12-C12.

EXAMPLE 7

Identification of Useful Hybridomas

Figure 8:
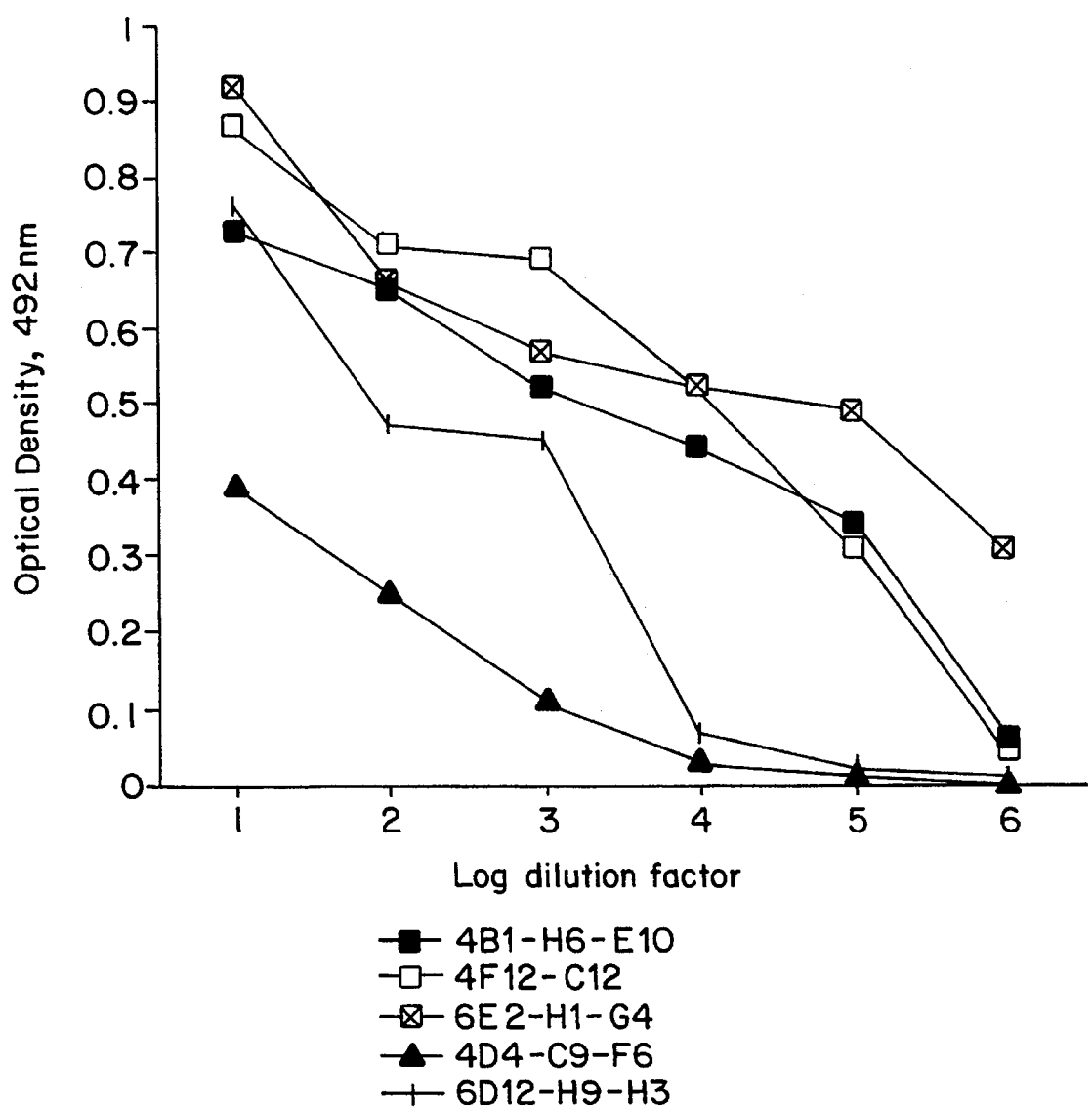
FIG. 8 is a graphic illustration of the binding profile of the monoclonal antibodies from the hybridoma cell lines 4B1-H6-E10, 4F12-C12, 6E2-H1-G4, 4D4-C9-F6 and 6D12-H9-G3, polyacrylate conjugated to bovine serum albumin (35K-BSA)

Monoclonal antibodies produced by five cell lines were assayed by indirect ELISA for binding to polyacrylate-BSA conjugates. The five cell lines tested were: 481-H6-E10, 4F12-C12, 6E2-H1-G4, 4D4-C9-F6 and 6D12-H9-G3. These assays were performed in duplicate and the results of the assays are summarized in FIG. 8.

EXAMPLE 8

Antibody Scale-up

Hybridoma cell lines 6E2-H1-G4 and 4H2-C12 were scaled up by growing them in vitro for several passages and injecting them into a group of pristane-primed Balb/c mice. The cells grew as ascites tumors in these mice and the resultant fluid accumulated in their peritoneal cavities was harvested. The ascites fluid was enriched in the desired anti-polyacrylate antibody which was purified and used in the assays described below.

EXAMPLE 9

Antibody Purification

Depending on the assay format being pursued, antibodies will be required either as unpurified ascites or as a highly purified immunoglobulin preparation. Antibodies were purified from ascites fluid by a variety of methods, depending on the antibody isotype and the sensitivity of the antibody to various buffers. The clones 6E2-H1-G4 and 4F12-C12 identified in Example 7 and 8 are of the IgG isotype, and accordingly, they were purified by using the pseudo-affinity matrix Protein A.

EXAMPLE 10

Reactivity Profile of the Anti-polyacrylate Monoclonal Antibodies

The binding specificity of the different anti-polyacrylate monoclonal antibodies was tested by an indirect ELISA. Replicate wells were coated with 500 ng per well of the following panel of antigens: BSA-polyacrylate, polyacrylate, or BSA. Serial dilutions of the ascites fluid ranging from 1:10 to $1:10^6$ in steps of 10 were incubated with the various antigen coated plates. After an incubation with the ascites fluid samples, the plates were washed and incubated with HRP-labelled goat anti-mouse Ig. Finally, the quantity of enzyme (HRP) retained in each well was quantified using $H_2O_2$ and a chromogenic substrate. The optical density readout at 492 mm was recorded using an automated ELISA reader and the results are summarized in FIGS. 9 and 10.

EXAMPLE 11

Monoclonal Antibodies Specific For SCP

Table 4 summarizes the binding data for the different hybridoma cell lines that were developed. All the cell lines were subcloned by limiting dilution in the presence of appropriate growth factors. When clonal populations of cells were identified, the supernatants were assayed again for SCP binding and single colonies that exhibited the required binding specificity were expanded and frozen down.

TABLE 4

| Anti-SCP Hybridomas, Binding Data | | | | |
|---|---|---|---|---|
|  |  | ELISA Signal of parents | | ELISA Signal of clone | |
| No. | Cell line | SCP | CP | SCP | CP |
| 1 | 6D12 H9-H3 | 1.70 | 0.11 | 1.48 | 0.02 |
| 2 | 6C8-F1-F9 | 0.92 | 0.02 | 0.77 | 0.00 |
| 3 | 4D4-C9-F6 | 0.77 | 0.18 | 0.61 | 0.12 |
| 4 | 6E2-H1-G4 | 2.00 | 0.11 | 1.81 | 0.45 |

TABLE 4-continued

Anti-SCP Hybridomas, Binding Data

| No. | Cell line | ELISA Signal of parents | | ELISA Signal of clone | |
| --- | --- | --- | --- | --- | --- |
| | | SCP | CP | SCP | CP |
| 5 | 4B1-H6-E10 | 1.39 | 0.50 | 1.74 | 0.55 |
| 6 | 4F12-C12 | 1.46 | 0.16 | 1.48 | 1.38 |

EXAMPLE 12

Cross-reactivity Profile of the Anti-SCP Monoclonal Antibodies

The binding specificity of the different anti-SCP monoclonal antibodies was tested by an indirect ELISA. Replicate wells were coated with 500 ng per well of the following panel of antigens: BSA-SCP, BSA-CP, SCP or BSA. Serial dilutions of the ascites fluid ranging from 1:10 to $1:10^6$ in steps of 10 were incubated with the various antigen coated plates. After an incubation with the ascites fluid samples, the plates were washed and incubated with HRP-labelled goat anti-mouse Ig. Finally, the quantity of enzyme (HRP) retained in each well was quantified using $H_2O_2$ and a chromogenic substrate. The optical density readout at 492 mn was recorded using an automated ELISA reader and the results are summarized in FIGS. 1, 2, and 3.

Figure 1:
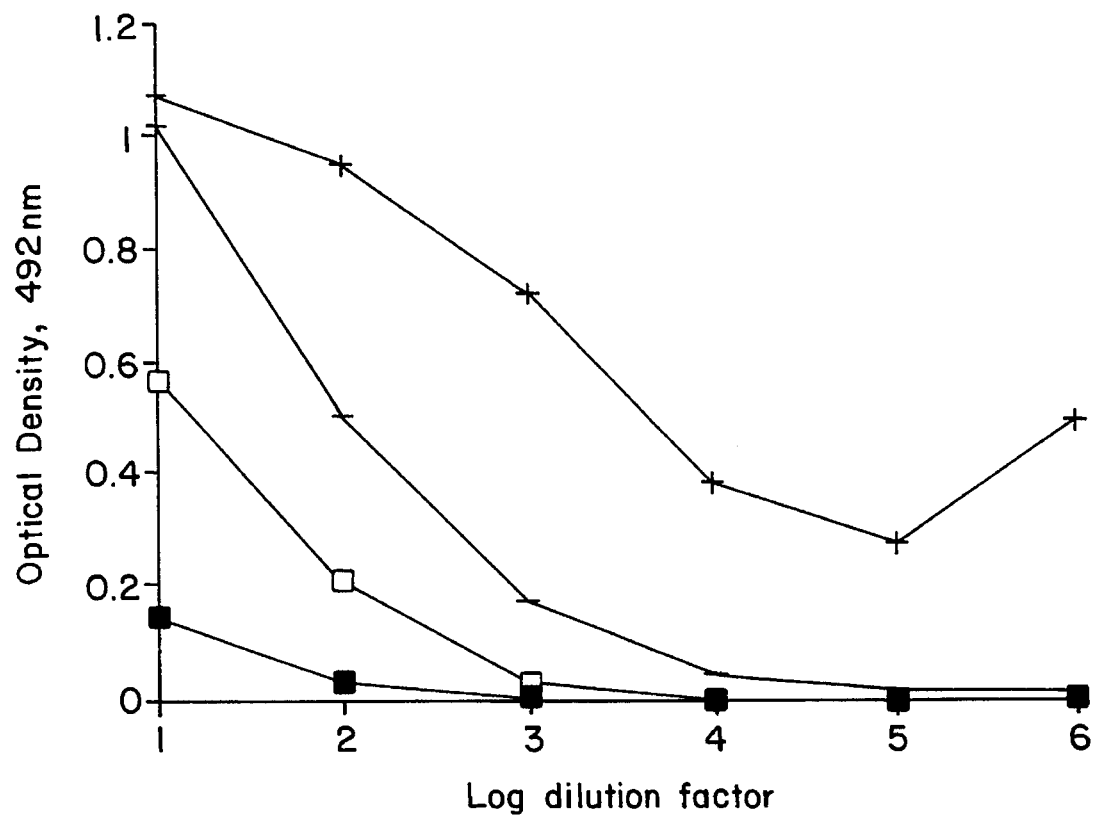
FIG. 1 is a graphic illustration of the binding profile of the monoclonal antibody from hybridoma cell line 6E2-H1-G4 to the sulfonated copolymer of acrylic acid and acrylamide conjugated to bovine serum albumin (BSA-SCP) +, the non-sulfonated copolymer of acrylic acid and acrylamide conjugated to bovine serum albumin (BSA-CP) -, the sulfonated copolymer of acrylic acid and acrylamide (SCP) ■, and to a control bovine serum albumin (BSA) □.
Figure 2:
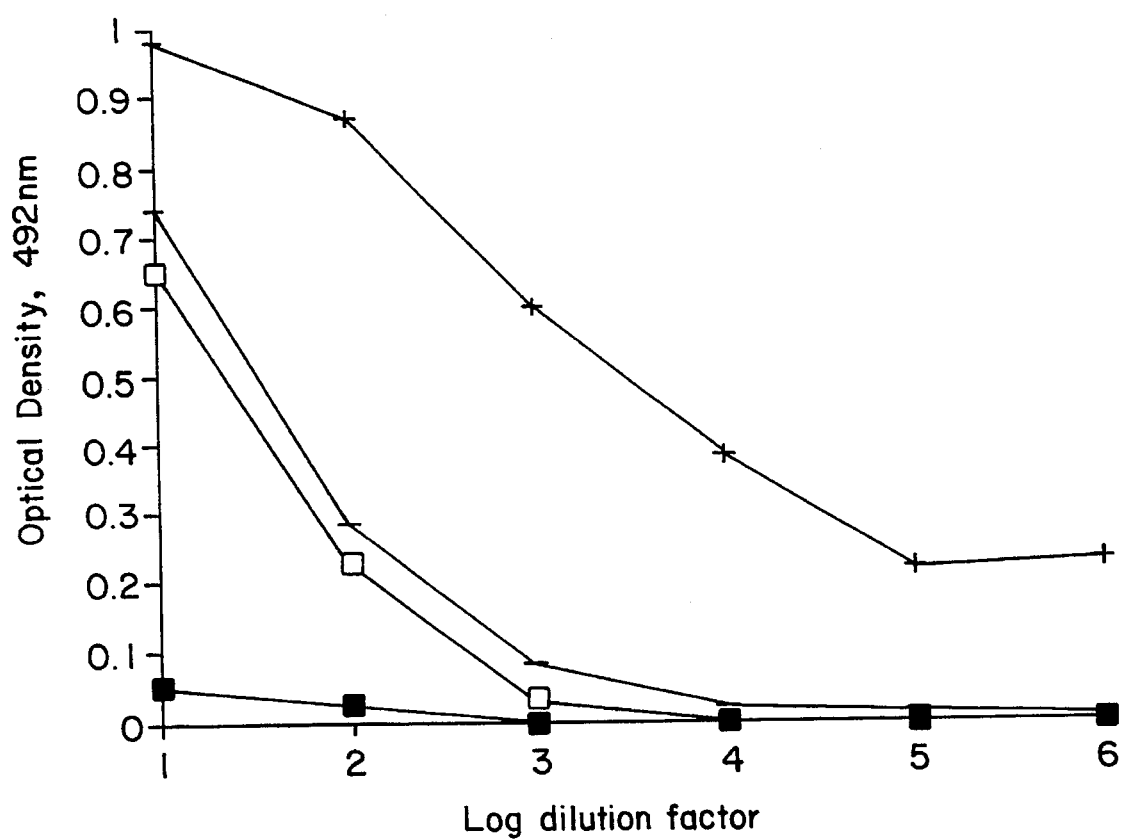
FIG. 2 graphically illustrates the binding profile of the monoclonal antibody from the hybridoma cell line 6D12-H9-G3 to BSA-SCP +, BSA-CP -, SCP ■, and BSA □.
Figure 3:
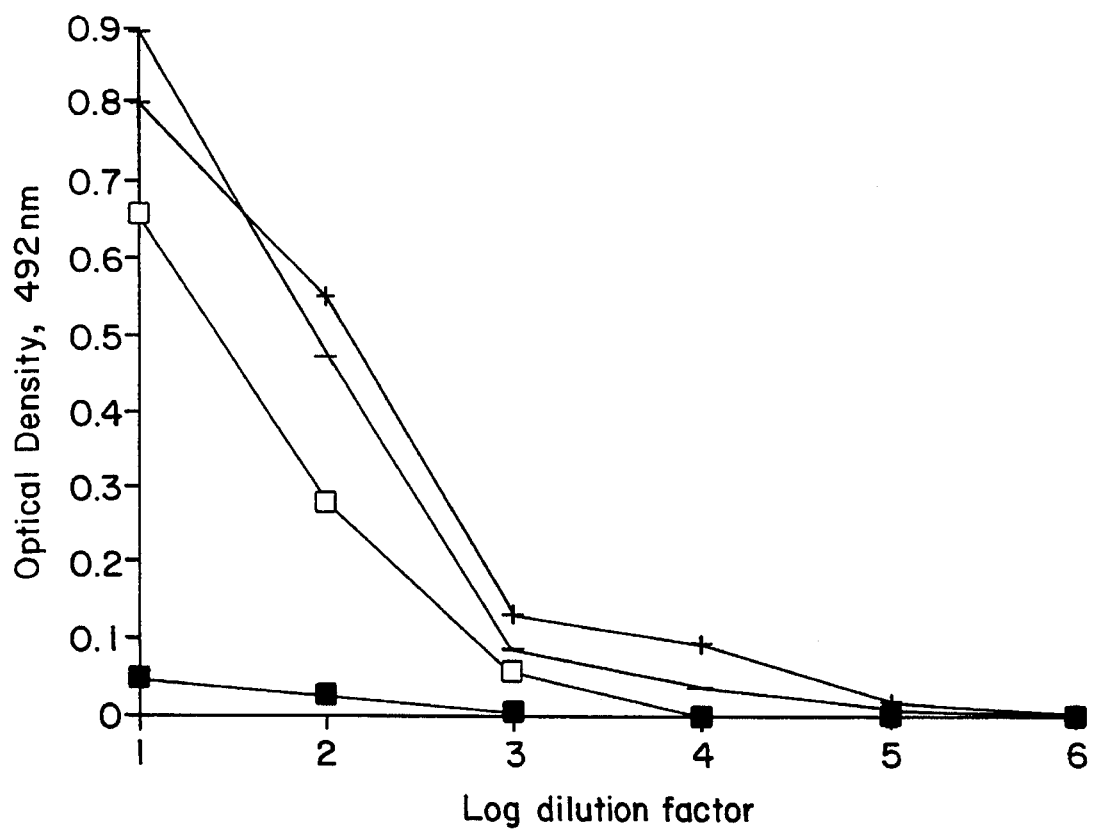
FIG. 3 is a graphic illustration of the binding profile of the monoclonal antibody from hybridoma cell line 4D4-C9-F6 to BSA-SCP +, BSA-CP =, SCP ■, and BSA □.

Of the three different monoclonal antibodies whose results are shown in FIGS. 1, 2, and 3, cell lines 6E2-H1-G4 and 6D12-H9H-3 show a dramatically higher binding specificity for BSA-SCP as compared to BSA-CP whereas cell line 4D4-C9-F6 is almost equally reactive to BSA-SCP and BSA-SP. These results confirm the earlier findings shown in Table 4, where these studies were carried out with spent tissue culture supernatants from these cell lines.

EXAMPLE 13

Specificity of Anti-SCP Monoclonal Antibodies 6E2-H1-G4 and 6D12-H9-H3 as Evaluated By Inhibition Assays Based on the information obtained from the indirect ELISA results, summarized in FIGS. 1, 2, and 3, two of the cell lines 6E2-H1-G4 and 6D12-H9-H3 which produced monoclonal antibody that showed specificity to BSA-SCP are the preferred cell lines of the invention. The results for the indirect ELISA were used to calculate the optimal concentrations of the two different monoclonal antibodies which would produce the most sensitive results in an inhibition ELISA. The inhibition ELISA carried out in this set of experiments is briefly described below.

Figure 4:
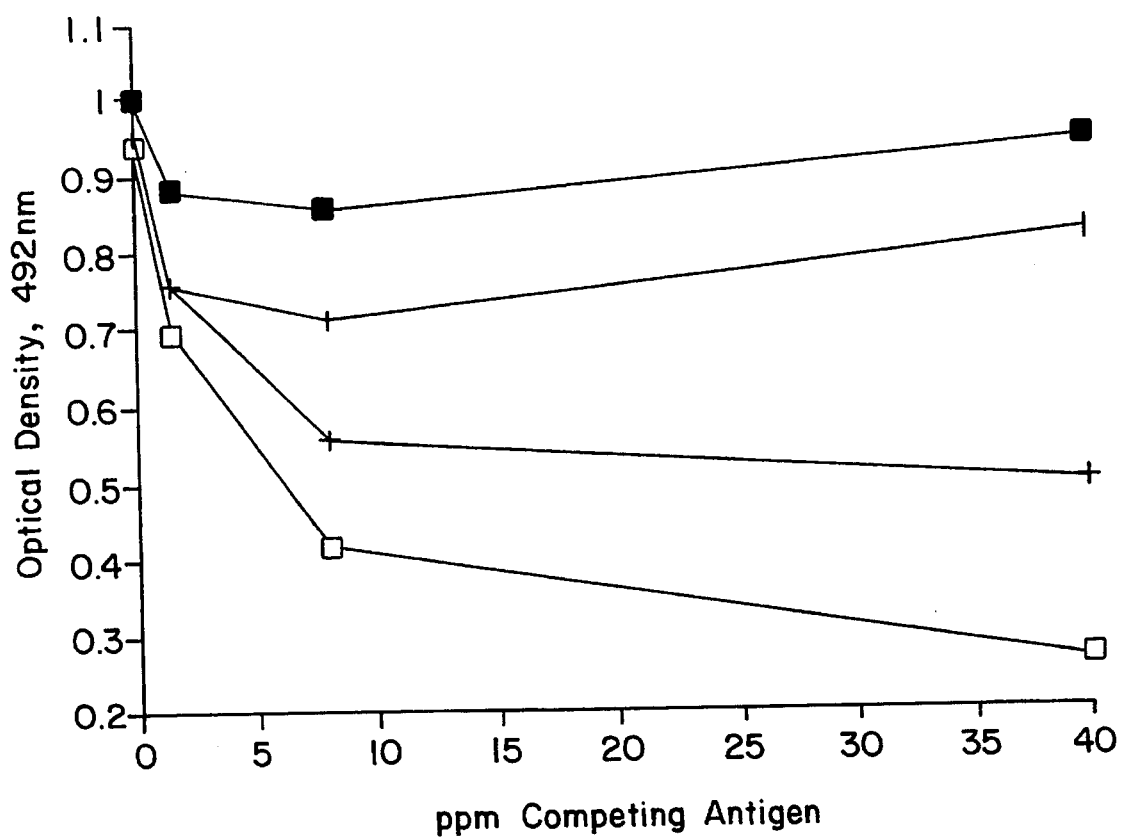
FIG. 4 is a graphic illustration of an inhibition Enzyme linked Immunosorbent Assay (ELISA) assay using the monoclonal antibody from the hybridoma cell line 6D12-H9-G3, wherein ■ is BSA, +, is CP, ┃ is SCP, and □ is BSA-SCP.
Figure 5:
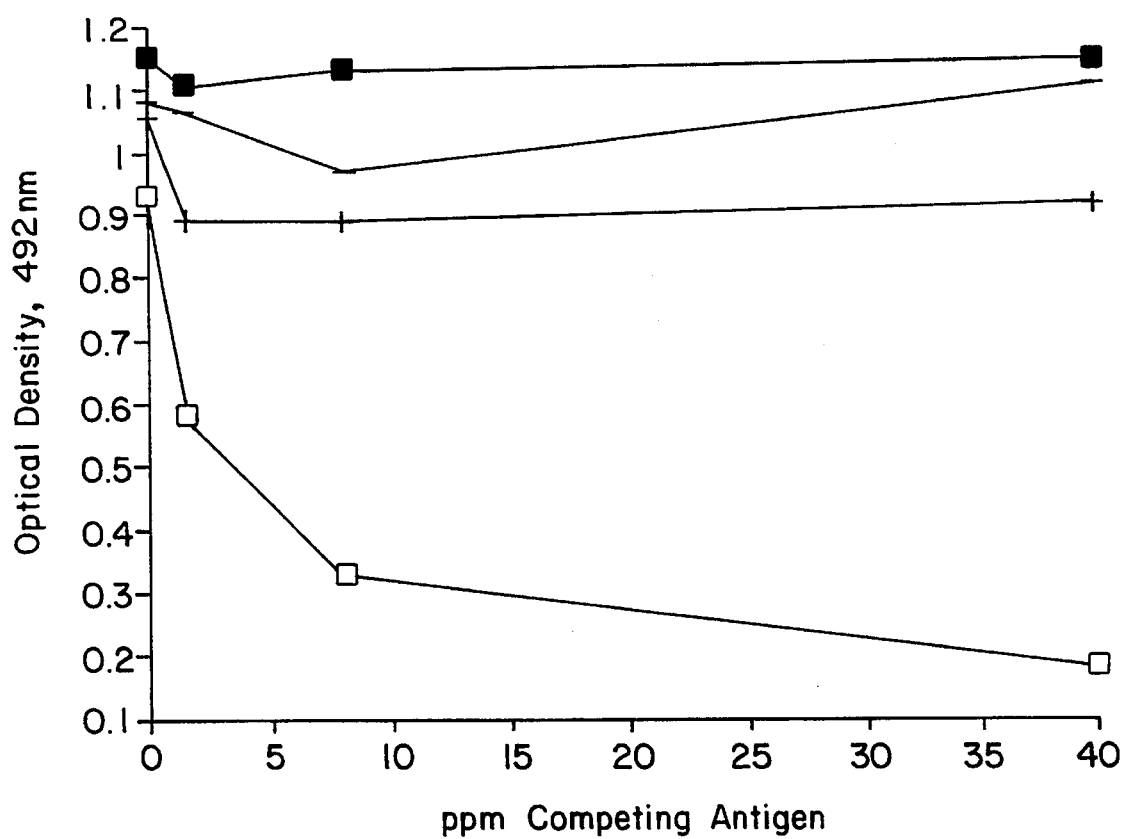
FIG. 5 is a graphic illustration of an inhibition ELISA assay using the monoclonal antibody from the hybridoma cell line 6E2-H1-G4, wherein ■ is BSA, - is CP, + is SCP, and □ is BSA-SCP.

Microtiter plates were coated with 500 ng per well of BSA-SCP and non-specific sites on the plate were blocked. Replicate samples of the test ascites fluid at a fixed concentration were preincubated with increasing concentrations of a panel of competing antigens for 2 hrs at room temperature. After this preincubation, the antibodies were allowed to bind to the BSA-SCP coated plates. The panel of antigens used in the competition ELISA included BSA-SCP, SCP, CP or BSA. The object of the assay was to demonstrate the antibody specificity in a solution phase assay. A highly specific antibody would bind tightly with the cognate antigen in solution and not the others. This would result in an inhibition of the antibody from binding to the BSA-SCP coated plate only in the presence of the appropriate antigen and not the others. The quantity of anti-SCP monoclonal antibody bound to the BSA-SCP coated plate was determined as before with the use of an HRP-labelled goat anti-mouse Ig and a chromogenic substrate for HRP. Results of such assays are shown in FIGS. 4 and 5. As seen from these figures, the two cell lines 6E2-H9-G4 and 6D12-H9-H3 do show considerable differences in the inhibition ELISA. Cell line 6D12-H9-H3 (shown in FIG. 4) detects approximately 5 to 40 ppm of SCP and distinguish it from CP. Cell line 6E2-H1-20G4, as shown in FIG. 5, was not as sensitive, but could still be useful in an assay. All of the above assays were performed in phosphate buffered saline, pH 7.2.

EXAMPLE 14

Assay of Simulated Field Samples

Various aqueous samples containing SCP, acquired from Nalco Chemical Company, Naperville, Ill., under the trademark designation PRISM® polymer, were prepared. Some of the samples mimicked "field" conditions in that they contained fairly high concentrations of $Fe^{+3}$ and $Ca^{+2}$ ions such that the SCP was substantially inactive. Also tested were samples which contained quantities of uncomplexed active SCP sufficient enough to prevent scaling.

Figure 6:
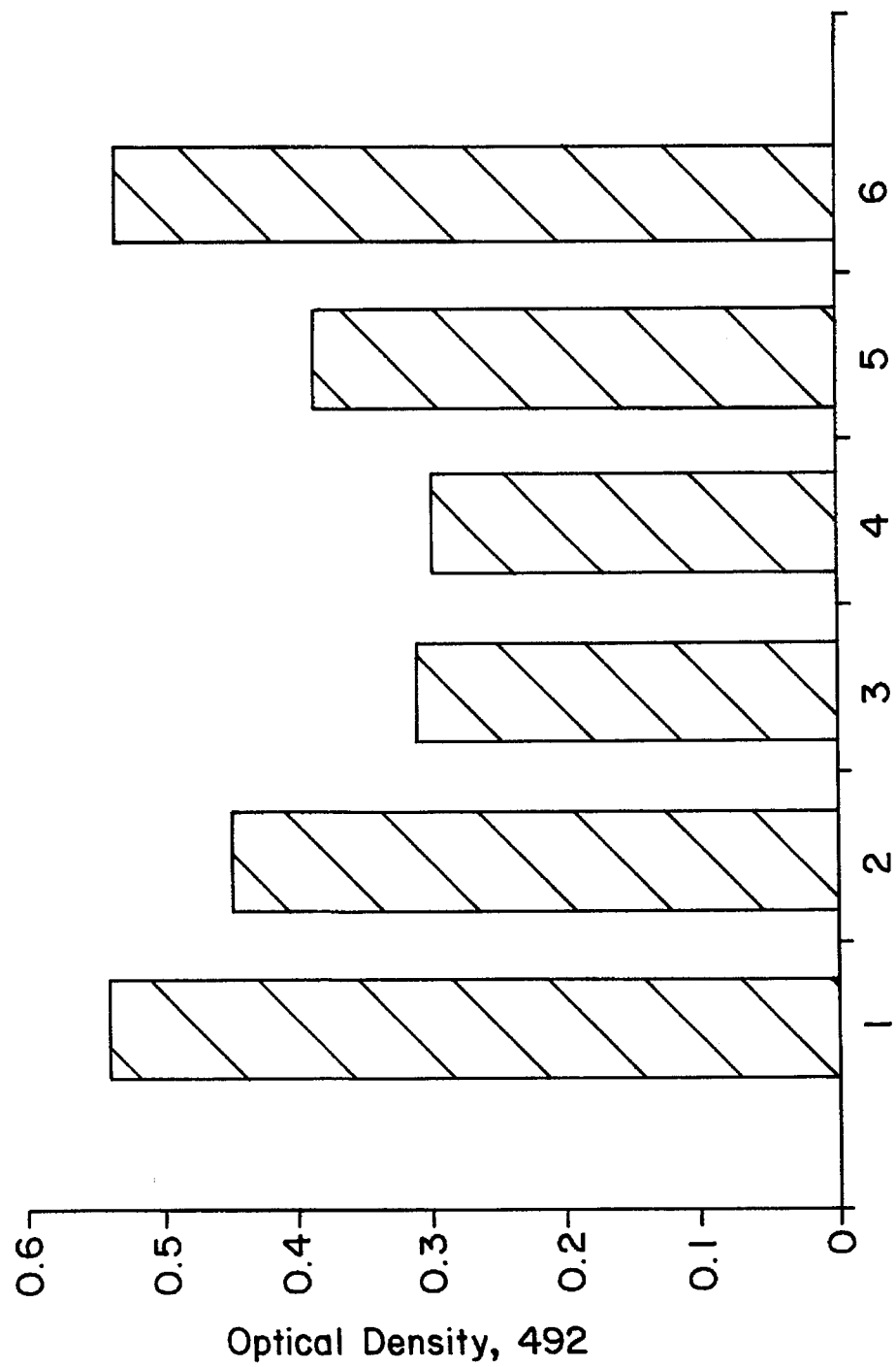
FIG. 6 is a graphic illustration of an inhibition ELISA assay using the monoclonal antibody from the hybridoma cell line 6D12-H9-G3 to detect active and inactive SCP in Phosphate Buffered Saline (PBS) buffer, wherein group 1 includes only PBS, group 2 includes 10 ppm CP, group 3 includes 10 ppm SCP, group 4 includes 20 ppm SCP, group 5 includes 10 ppm SCP, and group 6 includes 10 ppm inactive SCP and 4 mMFe.
Figure 7:
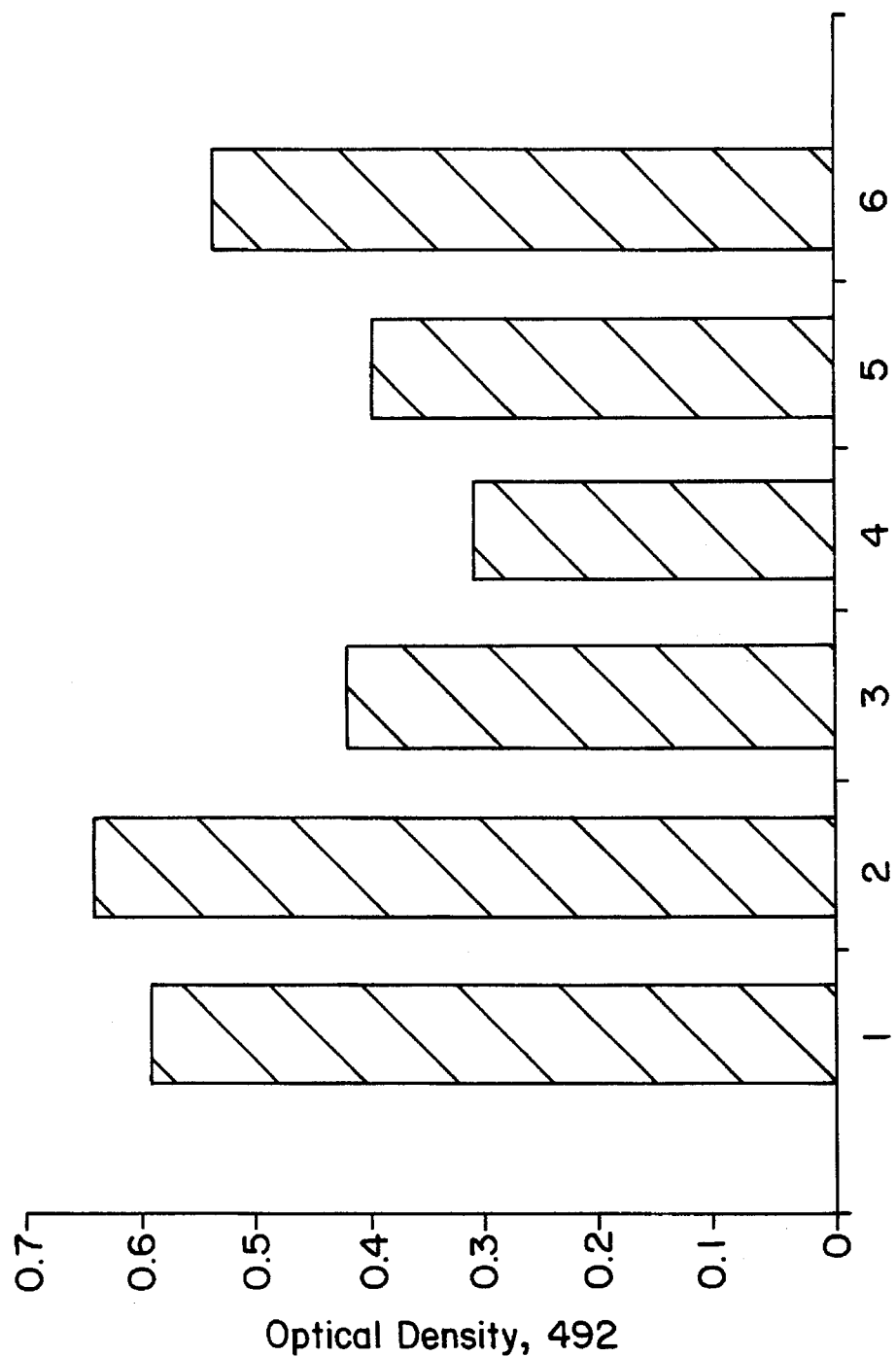
FIG. 7 is a graphic illustration of an inhibition ELISA assay using the monoclonal antibody from the hybridoma cell line 6D12-H9-G3 to detect active and inactive SCP in Tris Buffered Saline (TBS) buffer, wherein group 1 includes only TBS, group 2 includes 10 ppm CP, group 3 includes 10 ppm SCP, group 4 includes 20 ppm SCP, group 5 includes 10 ppm SCP, and group 6 includes 10 ppm inactive SCP and 4 mMFe.

A series of experiments were carried out to determine if the monoclonal antibodies of the invention could distinguish between an "active" and an "inactive" solution of SCP. Results of these experiments are shown in FIGS. 6 and 7. Parallel experiments were also carried out using phosphate buffered saline (PBS) and Tris buffered saline (TBS). As seen from FIGS. 6 and 7, the assay effectively distinguished between an "active" sample (sample 4) and an "inactive" sample (sample 6). In experiments shown in FIG. 6, the assays were carried out in PBS, whereas those shown in FIG. 7 utilized TBS. Samples 3 and 2, the positive and negative controls, contained 10 ppm of the SCP polymer and CP polymer respectively, and were made up in the respective buffers PBS and TBS. The samples were all diluted 1:2 with the appropriate buffer in the assay, either PBS or TBS, and were composed of the following: Sample 1 included only PBS. Sample 4 contained 20 ppm of SCP and hence should be an "active" sample, in as much as it contained quantities of SCP sufficient enough to prevent scaling. Sample 5 contained 10 ppm of SCP and could also be considered "active" although with a lower polymer concentration. Sample 6 was prepared with 10 ppm SCP and 4 mM $Fe^{+3}$ in such a way to simulate an "inactive" sample. Sample 6 presumably will not prevent scaling and clearly could be identified as not containing any detectable quantity of free, active SCP.

Figure 9:
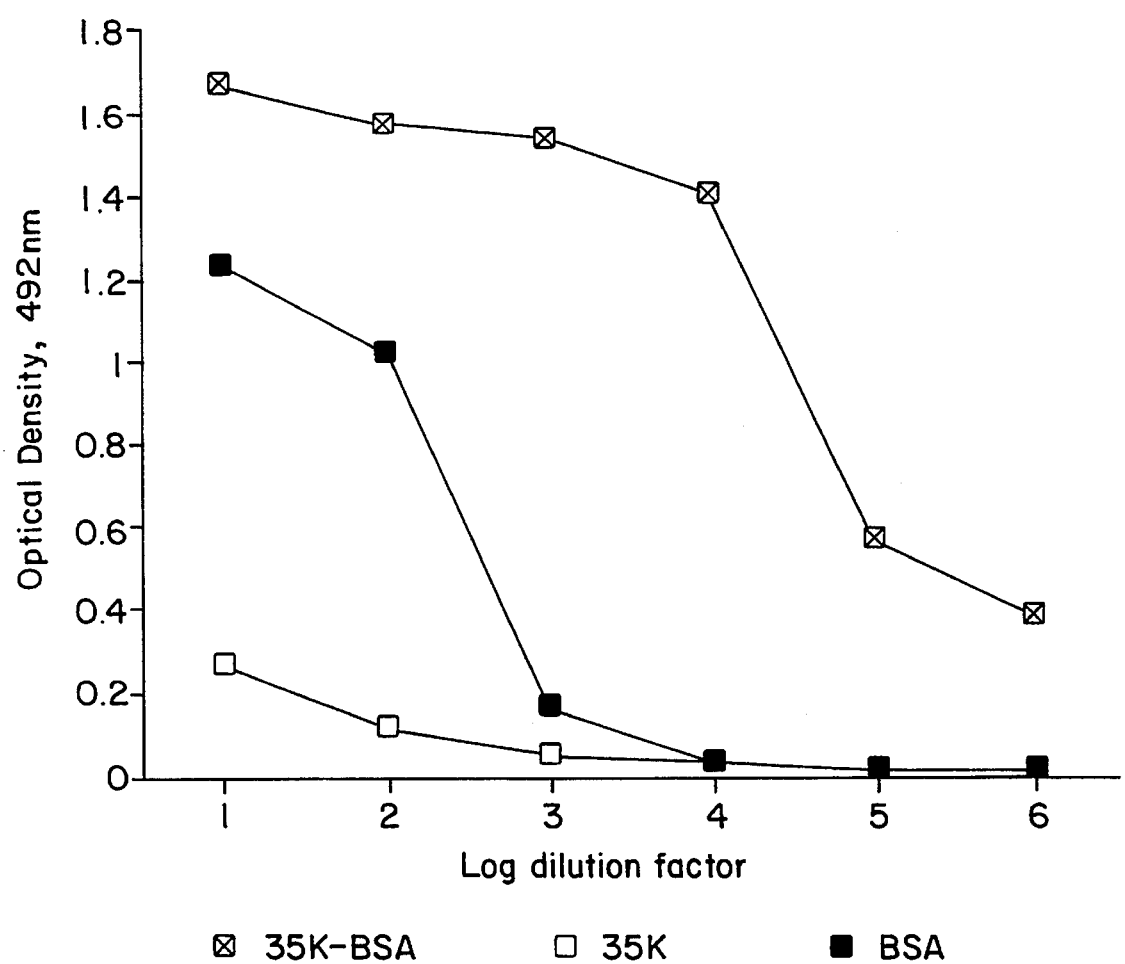
FIG. 9 graphically illustrates the binding profile of the monoclonal antibody from the hybridoma cell line 6E2-H1-G4 to 35K-BSA ⊠, 35K □, and BSA ■.
Figure 10:
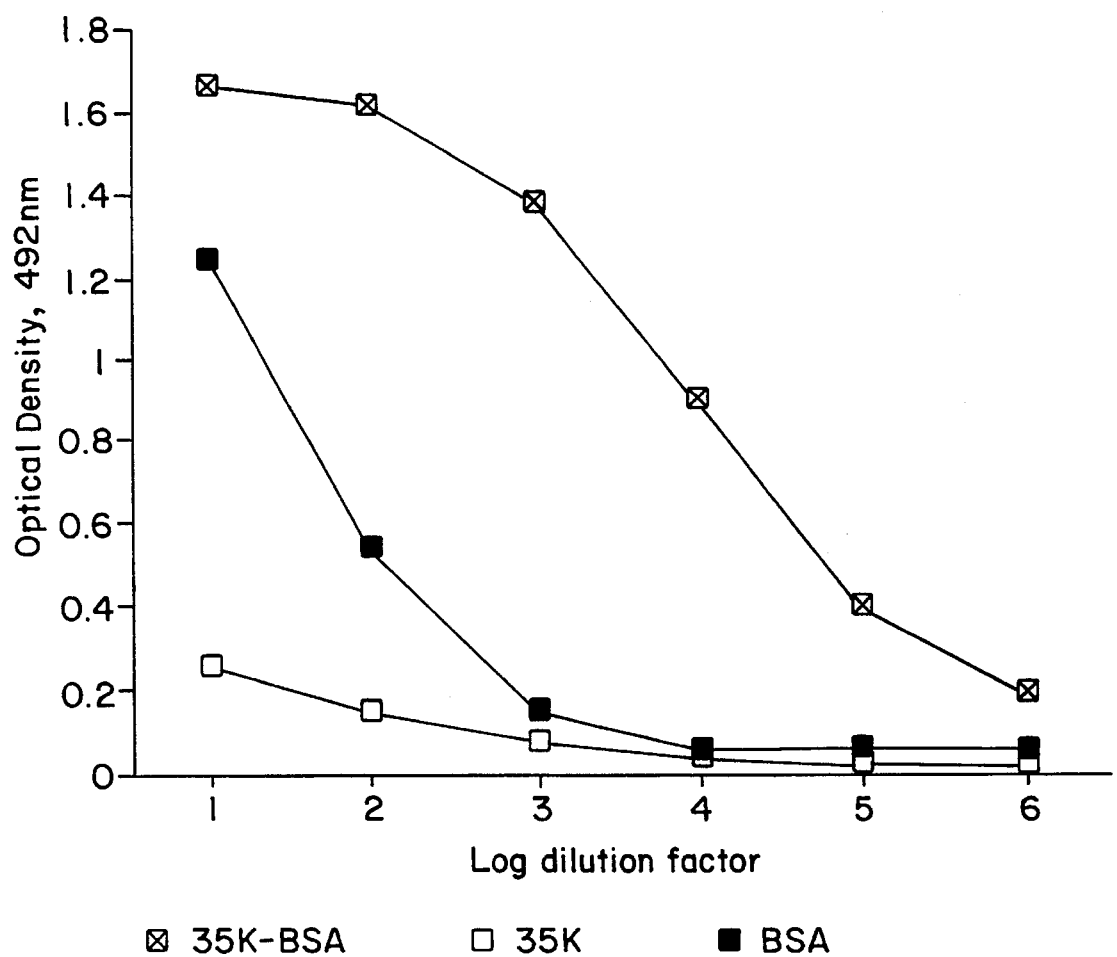
FIG. 10 is a graphic illustration of the binding profile of the monoclonal antibody from hybridoma cell line 4F12-C12 to 35K-BSA ⊠, 35K □, and BSA ■.

Of the two different monoclonal antibodies whose results are shown in FIGS. 9 and 10, cell lines 6E2-H1-G4 and 4F12-C12 show a dramatically higher binding specificity for BSA-polyacrylate as compared to BSA or polyacrylate alone. These results confirm the earlier findings shown in FIG. 8, where these studies were carried out with tissue culture supernatants from these cell lines.

What is claimed is:

1. A method for the determination of the concentration of a water soluble, vinyl polymer used to prevent corrosion and mineral deposits in a container of water employed for industrial purposes, said process comprising the steps of:

(a) incubating a sample of water obtained from an industrial container, said sample having been treated with the polymer to prevent corrosion and mineral deposits prior to obtaining said sample, with a monoclonal antibody having an affinity for the polymer said affinity being strong enough to recognize the polymer and to differentiate it from other polymers in the sample; and (b) detecting and measuring the degree of the binding of the monoclonal antibody from which the concentration of said polymer can be determined.

2. The method of claim 1, wherein the polymer is a sulfonated copolymer of polyacrylic acid and acrylamide, and the container is an industrial cooling water tower.

3. The method of claim 1, wherein the polymer is polyacrylate, and the container is an industrial boiler.

4. The method of claim 1, wherein the antigen-antibody binding is detected and measured by an enzyme-linked immunosorbent assay.

5. The method of claim 1, wherein the monoclonal antibody is bound to a solid carrier.

6. The method for the determination of the concentration of a water soluble, vinyl polymer of claim 1, wherein the container of water is a metal container.

7. A method for the determination of the concentration of a polymer in a industrial water sample, the method including the step of incubating a sample of the fluid containing the polymer with a monoclonal antibody having an affinity for the polymer said affinity being strong enough to recognize the polymer and to differentiate it from other polymers in the sample, and detecting and measuring the degree of the binding of monoclonal antibody, from which the presence of the polymer can be inferred and concentration of said polymer can be determined.

8. The method of claim 7, wherein the antigen-antibody binding is detected and measured by an enzyme-linked immunosorbent assay.

9. The method of claim 8, wherein the antibody is bound to a solid carrier.

10. A kit for the detection and quantitation of a vinyl, water soluble polymer in an industrial water sample, said kit providing an environment in which an antigen-antibody complex occurs between a polymer present in a sample of water to be tested and a monoclonal antibody provided in the kit, said kit comprising:

(a) a monoclonal antibody which specifically binds to the polymer; and (b) components which provide an observable reaction from which complexing of the monoclonal antibody to the polymer is inferred.

11. The kit of claim 10, wherein the water soluble, vinyl polymer is a sulfonated copolymer of polyacrylic acid and polyacryamide.

12. The kit of claim 10, wherein the water-soluble vinyl polymer is polyacrylate.

13. The kit of claim 10, wherein the observable reaction is an enzyme linked immunoassay.

14. The kit of claim 10, wherein the observable reaction occurs on a solid support.

* * * * *